United States Patent [19]

Houminer et al.

[11] Patent Number: 5,120,368
[45] Date of Patent: Jun. 9, 1992

[54] VANILLIN 5-HYDROXYESTERS AND SMOKING COMPOSITIONS CONTAINING A VANILLIN-RELEASE ADDITIVE

[75] Inventors: Yoram Houminer; Kenneth F. Podraza; Everett W. Southwick, all of Richmond, Va.

[73] Assignees: Philip Morris Incorporated, New York, N.Y.; Philip Morris Products, Inc., Richmond, Va.

[21] Appl. No.: 565,127

[22] Filed: Aug. 10, 1990

[51] Int. Cl.$^5$ ............................ A24B 3/12; C07C 69/76
[52] U.S. Cl. ........................................ 131/276; 560/109
[58] Field of Search ...................... 131/276, 277, 278; 560/109

*Primary Examiner*—V. Millin
*Attorney, Agent, or Firm*—James E. Schardt; George A. Depaoli

[57] ABSTRACT

This invention provides novel vanillyl 5-hydroxyesters, and smoking compositions which contain a vanillyl 5-hydroxyester as a flavorant-release additive.

Under cigarette smoking conditions, a combustible filler and/or paper wrapper additive such as 4'-formyl-2'-methoxyphenyl 5-hydroxy-2-isopropylhexanoate pyrolyzes into vanillin and 2-isopropyl-5-hydroxyhexanoic acid delta lactone flavorants as volatile components of the cigarette smoke.

18 Claims, No Drawings

VANILLIN 5-HYDROXYESTERS AND SMOKING COMPOSITIONS CONTAINING A VANILLIN-RELEASE ADDITIVE

CROSS-REFERENCE TO RELATED APPLICATIONS

The subject matter of the present invention is related to that disclosed in patent application Ser. Nos. 537,775, filed Jun. 13, 1990; 565,126, filed Aug. 10, 1990; 613,013, filed Nov. 15, 1990; 660,881, filed Feb. 26, 1991; and 688,436, filed Apr. 22, 1991.

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; 3,379,754; 4,036,237; 4,473,085; and the like.

J. C. Leffingwell et al "Tobacco Flavoring For Smoking Products" (R. J. Reynolds publication, 1972) recites a listing of desireable flavorants for smoking compositions, which include phenols, terpenols and lactones such as guaiacol, 1-undecanol and 5-dodecalactone.

U.S. Pat. No. 3,251,366 describes tobacco products that contain a lactone flavorant additive such as $\alpha,\beta$-dimethyl-$\gamma$-pentyl-$\gamma$-hydroxybutenolide which imparts a celery-like note to mainstream smoke.

U.S. Pat. Nos. 3,372,699 and 3,372,700 describe the use of a lactone such as $\beta$-methylbutyrolactone or 4-hydroxy-4-methyl-5-hexenoic acid $\beta$ lactone as a flavorant additive in tobacco products.

U.S. Pat. Nos. 3,380,457; 3,563,248; and 3,861,403 describe other lactones which are recommended for use as flavorant additives in tobacco products, such as $\beta$-methyl-$\delta$-valerolactone, 3-(2-hydroxycyclohexyl)propionic acid $\delta$ lactone, 4-methyl-6-n-pentyl-$\alpha$-pyrone, and the like.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as 1-menthyl linalool carbonate. Under smoking conditions pyrolysis of the carbonate ester releases menthol which flavors the mainstream smoke.

U.S. Pat. Nos. 3,332,428 and 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,117,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

Tobacco Patents, Supplement No. 88/1 (N. & D. J. Foster, Southhampton, England) reports a R&D Disclosure by Philip Morris Inc., that describes 5-hydroxyester compounds such as 2-methoxy-4-methylphenyl 2-isopropyl-5-hydroxyhexanoate which are utilized as smoking composition additives, and which under normal smoking conditions release lactone and alcohol flavorants into cigarette smoke.

Of specific interest with respect to the present invention is the proposed utilization of an organic additive to a cigarette paper wrapper to enhance sidestream smoke aroma under smoking conditions. U.S. Pat. No. 4,804,002 describes a tobacco product wrapper containing a flavorant glycoside additive comprising an acetal of a carbohydrate and phenolic compound. Under cigarette smoking conditions a flavorant additive such as ethyl vanillyl-D-glucoside yields ethyl vanillin and levoglucosan as volatile pyrolysis products.

There is continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having incorporated therein a flavorant-release additive which under normal smoking conditions imparts improved aroma to sidestream smoke.

It is a further object of this invention to provide novel ester compounds which are adapted to be incorporated into cigarette filler and/or paper wrapper components, and which under normal smoking conditions release volatile lactone and vanillin flavorants into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.000–5 weight percent, based on the total weight of filler, of a flavorant-release additive corresponding to the formula:

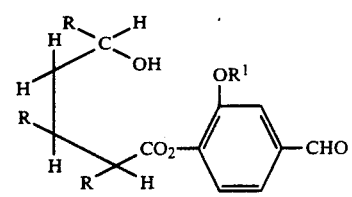

where R is hydrogen or a $C_1$–$C_4$ alkyl substituent; and $R^1$ is methyl or ethyl.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

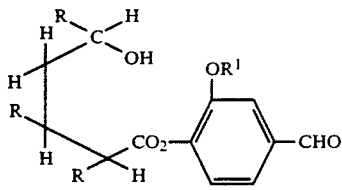

where R is hydrogen or a $C_1$–$C_4$ alkyl substituent; and $R^1$ is methyl or ethyl.

Illustrative of $C_1$–$C_4$ alkyl substituents in the above represented flavorant-release additive formula are methyl, ethyl, propyl, 2-propyl, butyl, 2-butyl and isobutyl groups.

A cigarette smoking product in accordance with the present invention typically contains between about 0.01–5 weight percent of flavorant release additive in the paper wrapper.

In a further embodiment an invention cigarette product contains between about 0.01–5 weight percent of flavorant-release additive in the paper wrapper, and contains between about 0.0001–5 weight percent of flavorant-release additive in the combustible filler, based on the weight of filler.

A present invention flavorant-release additive which is incorporated in smoking compositions as described above is a low volatility compound which under normal smoking conditions pyrolyzes into two volatile constituents, both of which enhance the flavor and aroma of low delivery cigarette smoke:

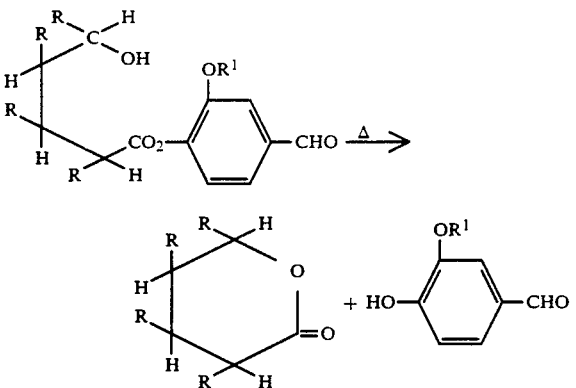

where R and $R^1$ are as previously defined.

An important feature of an invention smoking composition is the release of two flavorants under smoking conditions, one of which is a lactone and the other is vanillin or ethyl-vanillin.

Both the lactone and vanillin volatiles which are released have exceptional organoleptic properties. Each of the compounds contributes a pleasant flavor and aroma to cigarette smoke.

Preparation of Flavorant-release Compounds

The flavorant-release compounds of the present invention are vanillyl 5-hydroxyesters which can be prepared by a general procedure as represented in the following reaction diagram:

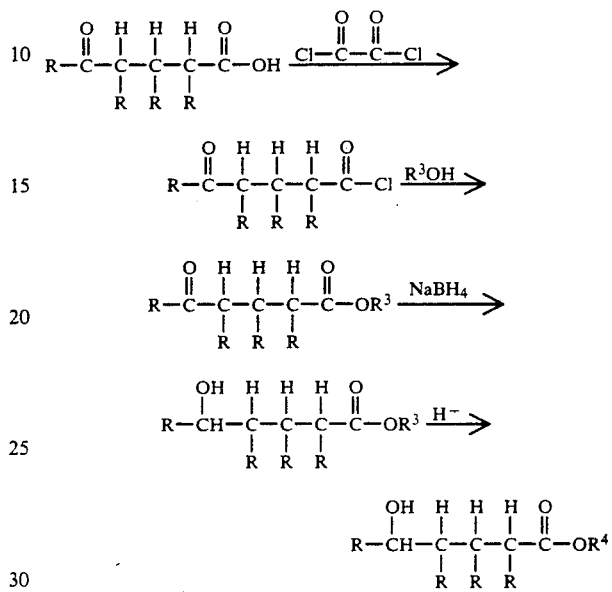

In the above formulas, $R^3$ is vanillin acetal or ethyl vanillin acetal, and $R^4$ is a vanillyl or ethyl-vanillyl ester radical after removal of the acetal protective functionality.

In another embodiment this invention provides a novel class of vanillyl 5-hydroxyesters corresponding to the formula:

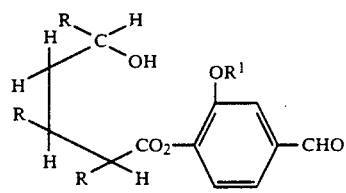

where R is hydrogen or a $C_1$–$C_4$ alkyl substituent; and $R^1$ is methyl or ethyl.

The novel vanillyl 5-hydroxyesters of the present invention are stable and odorless compounds at ambient temperatures. As demonstrated in Example VII, the invention vanillyl 5-hydroxyesters decompose at a relatively low pyrolysis temperature (e.g., 200° C.) to release a high yield of desirable flavor-enhancing lactone and vanillin or ethyl vanillin components in cigarette smoke.

The invention vanillyl 5-hydroxyesters are uniquely adapted to pyrolyze into a 100 percent yield of flavor-enhancing components under normal smoking conditions. As illustrated in Example VII, in contradistinction a closely related compound not in accordance with the present invention, i.e., 2'-methoxy-4'-methylphenyl 5-hydroxy-2-isopropylhexanoate, pyrolyzes to the extent of about a 16 percent yield of thermolysis products at 200° C.

Preparation of Tobacco Compositions

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to the formula:

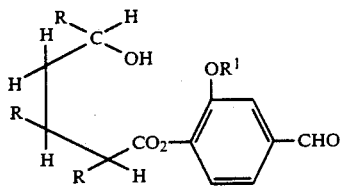

where R is hydrogen or a $C_1$–$C_4$ alkyl substituent; and $R^1$ is methyl or ethyl.

The invention, vanillyl 5-hydroxyester flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal cross-links causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

As previously described herein above, an invention flavorant-release additive also can be incorporated in the paper wrapper of cigarette products for the purpose of enhancing the aroma of cigarette sidestream smoke under smoking conditions.

The following Examples are further illustrative of the present invention. The specific ingredients and processing parameters are presented as being typical, and various modifications can be derived in view of the foregoing disclosure within the scope of the invention.

EXAMPLE I

The Example illustrates the preparation of reference compound 2'-methoxy-4'-methylphenyl 5-hydroxy-2-isopropylhexanoate.

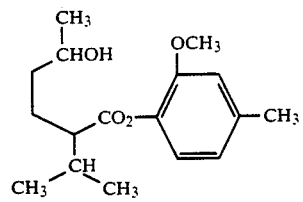

Procedure A

A solution of 6.0 g (0.0468 mole) of oxalyl chloride in 4 ml of benzene was chilled to 0° C under a nitrogen atmosphere. A solution of 4.0 g (0.0234 mole) of 2-isopropyl-5-oxohexanoic acid in 4 ml of benzene was added and the solution was warmed to room temperature, and stirred at room temperature for 20 hours. Evaporation of the solvent under reduced pressure yielded a 2-isopropyl-5-oxohexanoyl chloride residue, and the residue was dissolved in 3 ml of benzene. A 3.1 g (0.0222 mole) quantity of 2-methoxy-4-methylphenol in 5 ml of benzene was added, and the solution was stirred for 20 hours. Ether was added and the solution was washed with water, aqueous saturated sodium chloride, and 5% potassium hydroxide. The organic layer was dried over anhydrous calcium chloride, and the solvent was removed under reduced pressure to yield a liquid which was purified by Kugelrohr distillation bp 120°–125° C./0.04 mm Hg.

A solution of 0.5 g (1.7 mmoles) of the liquid 2'-methoxy-4'-methylphenyl 2-isopropyl-5-oxohexanoate intermediate in 2-propanol was chilled to 0° C. Sodium borohydride 16.3 mg (0.4 mmole) was added to the solution and stirred at 0° C. for 4 hours. Ether and aqueous saturated ammonium chloride were added. The organic layer was washed with water and then with aqueous saturated sodium chloride. The organic layer was dried over anhydrous magnesium sulfate, and evaporation of the solvent under reduced pressure yielded a liquid which was purified by preparative thin layer chromatography on silica gel using 15% acetone/hexane as the eluent. A 50 mg quantity of the pure product was obtained as an oil. NMR and IR spectra confirmed the title compound structure.

Anal. Calc. for $C_{17}H_{26}O_4$: C, 69.36; H, 8.90

Found: C, 69.19; H, 9.00

Procedure B

2'-methoxy-4'-methylphenyl 2-isopropyl-5-oxohexanoate was prepared in the manner described in the above procedure A.

A 500 mg sample of the keto-ester was added to a mixture of 5 ml of 95% ethanol, 50 mg of platinum oxide and 15 mg of sodium nitrite. The heterogeneous mixture was charged into a Parr Shaker and hydrogenated at 45 psi for 24 hours at 25° C. The mixture was filtered, and the filtrate was concentrated under reduced pressure, and the residual crude product was purified by chromatography on silica gel (20% ethyl acetate in hexane) to yield 200 mg (40% yield) of pure product, which was identical to that obtained by procedure A.

EXAMPLE II

This Example illustrates the preparation of reference compound 2'-methoxy-4'-propylphenyl 5-hydroxy-2-isopropylhexanoate.

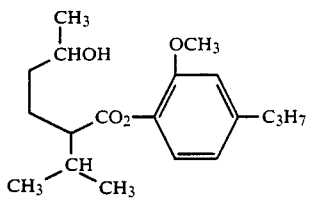

Following the steps of procedure B in Example I, the title compound was prepared by hydrogenation of 300 mg of 2'-methoxy-4'-allylphenyl 2-isopropyl-5-oxohexanoate. NMR and IR spectra confirmed the title compound structure.

Anal. Calc. for $C_{19}H_{30}O_4$: C, 70.79; H, 9.38;
Found: C, 70.5 ; H, 9.6.

EXAMPLE III

This Example illustrates the preparation of intermediate compound 4'-formyl-2'-methoxyphenyl 5-hydroxy-2-isopropylhexanoate propyleneglycol acetal.

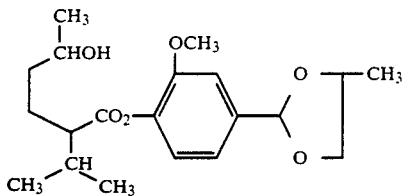

To a cold (0° C.) stirred suspension of 0.20 mole (34.4 g) of 2-isopropyl-5-oxohexanoic acid in 200 ml of hexane was added dropwise a solution of 0.22 mole (28 g) of oxalyl chloride in 200 ml of hexane. The reaction mixture was allowed to stand at room temperature for about 18 hours, then volatile materials were removed on a rotary evaporator. The residue was treated with 200 ml of hexane, and removal of the solvent provided 34.7 g of liquid acid chloride product.

A 1-liter 3-neck flask was charged with 10.56 g of sodium hydride (50% in mineral oil), and the mineral oil was removed by washing with hexane and drying under nitrogen. The resultant dry powder was cooled in an ice bath and suspended in ml of tetrahydrofuran. To the suspension was added dropwise a solution of 42 g (0.2 mole) of vanillin propyleneglycol acetal in 200 ml of tetrahydrofuran. The mixture was stirred at room temperature for 2 hours and then cooled in an ice bath and a solution of the above prepared acid chloride in 200 ml of tetrahydrofuran was added dropwise. The reaction mixture was stirred for about 18 hours at room temperature, and then concentrated to one-third its volume on a rotary evaporator and diluted with 700 ml water. The organic layer was removed and the aqueous layer was extracted with 3×200 ml of ether. The combined organic layers were washed with 250 ml of 10% sodium carbonate, 250 ml of water, and finally with 250 ml of saturated sodium chloride solution. After drying over sodium sulfate, the extract was concentrated on a rotary evaporator at 50° C. to provide 45.8 g of crude ester product. The ester was distilled in a Kugelrohr to yield 25.8 g of keto-ester as a pale yellow liquid, bp 125° C./50 mm Hg.

The keto-ester (25.8 g, 0.07 mole) was dissolved in 200 ml of 95% ethanol and the solution was cooled in an ice bath. Solid sodium borohydride (2.7 g, 0.07 mole) was added in portions over a period of 30 minutes. After addition was complete, the reaction medium was stirred for 1 hour at 0° C., and then quenched by adding 250 ml of saturated ammonium chloride solution. The mixture was diluted with 500 ml of water and extracted three times with 250 ml of ether. The combined extracts were washed with water until neutral, dried over sodium sulfate, and concentrated on a rotary evaporator to yield 34 g of a yellow viscous liquid. A pure sample of the acetal-protected hydroxyester product was obtained by column chromatography on silica gel with elution by 50% ethyl acetate/hexane. The structure of the title compound was confirmed by NMR and IR spectroscopy.

EXAMPLE IV

This Example illustrates the preparation of 4'-formyl-2-methoxyphenyl 5-hydroxy-2-isopropylhexanoate in accordance with the present invention.

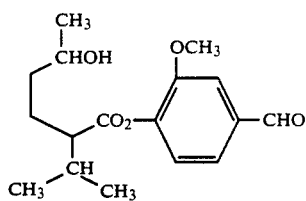

Acetal-protected hydroxy-ester (34 g) prepared in the manner described in Example III, was dissolved in 200 ml of acetone and water was added until the solution was cloudy, then several drops of dilute hydrochloric acid were added. After stirring at room temperature for one hour, the solution was concentrated on a rotary evaporator to remove most of the acetone. The residue was dissolved in 300 ml of ether, and washed with water and with 250 ml of saturated sodium chloride solution. The ether solution was dried over sodium sulfate, filtered and concentrated on a rotary evaporator to yield 26.3 g of crude product. A pure sample was obtained by preparative reverse-phase chromatography (55% acetonitrile-water). NMR and IR spectra confirmed the title compound structure.

Anal. Calc for $C_{17}H_{24}O_5$: C, 66.21; H, 7.84;
Found: C, 65.84; H, 7.96.

EXAMPLE V

This Example illustrates the preparation of 4'-formyl-2'-ethoxyphenyl 5-hydroxy-2-isopropylhexanoate.

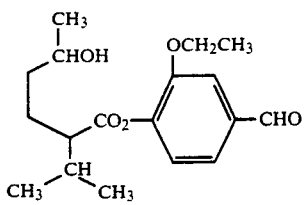

The synthesis of the title compound was conducted on a 0.1 mole scale following the steps described in Example IV, and utilizing an ethyl vanillin propylenglycol acetal intermediate. NMR and IR spectra confirmed the title compound structure.

EXAMPLE VI

This Example illustrates the preparation of 4'-formyl-2'-methoxyphenyl 5-hydroxy-3-methylhexanoate.

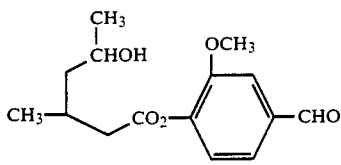

The synthesis of the tile compound was conducted on a 0.25 mole scale following the steps described in Example IV, and utilizing a 3-methyl-5-oxohexanoyl chloride intermediate. NMR and IR spectra confirmed the title compound structure.

EXAMPLE VII

This Example illustrates the thermolysis properties of an invention vanillin-release ester compound as compared to reference compounds.

The thermolysis study was conducted by heating a sample of test compound in a sealed tube at 200° C. for 15 minutes.

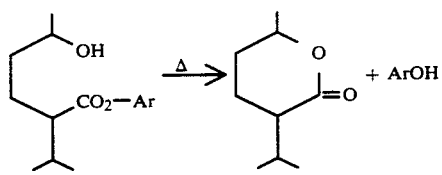

| Example Number Test Compound | Percent Thermolysis |
| --- | --- |
| IV | 100 |
| III | <50 |
| I | 16 |
| II | 9 |

The summarized data demonstrate that invention compound 4'-formyl-2'-methoxyphenyl 5-hydroxy-2-isopropylhexanoate (Example IV) pyrolyzes cleanly and quantitatively to vanillin and 2-isopropyl-5-hydroxyhexanoic acid delta lactone products.

In a further demostration, the Example IV invention compound in an ethanbolic solution was applied to the paper wrapper of cigarettes, in a quantity of about 800 ppm based on tobacco filler weight. After the solvent was removed by drying, the treated cigarettes containing the invention additive were evaluated by an experienced smoking panel. Compared to untreated control cigarettes, the treated cigarettes exhibited a sweet, herbal-spicy, vanillin aroma in the sidestream smoke, without a significant change in mainstream smoke flavor.

The delta lactone product released by pyrolysis of the Example IV compound is an identified trace constituent of smoking tobacco, and is known to exhibit a complex aroma described as sweet, fruity-floral, spicy-woody and herbal green.

What is claimed is:

1. A smoking composition comprising an admixture of
   (1) combustible filler selected from natural tobacco, reconstituted tobacco and tobacco substitutes, and
   (2) between about 0.0001-5 weight percent, based on the total weight of filler, of a flavorant-release additive corresponding to the formula:

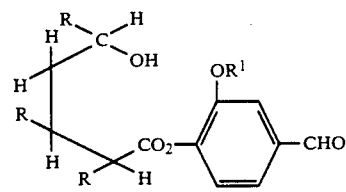

where R is hydrogen or a $C_1$-$C_4$ alkyl substituent; and $R^1$ is methyl or ethyl.

2. A smoking composition in accordance with claim 1 wherein the flavorant-release additive is 4'-formyl-2'-methoxyphenyl 5-hydroxy-2-isopropylhexanoate.

3. A smoking composition in accordance with claim 1 wherein the flavorant-release additive is 4'-formyl-2'-ethoxyphenyl 5-hydroxy-2-isopropylhexanoate.

4. A smoking composition in accordance with claim 1 wherein the flavorant-release additive is 4'-formyl-2'-methoxyphenyl 5-hydroxy-3-methylhexanoate.

5. A cigarette smoking product comprising (1) a combustible filler selected from natural tobacco, reconstituted tobacco and tobacco substitutes, and (2) a paper wrapper which has incorporated therein a flavorant-release additive corresponding to the formula:

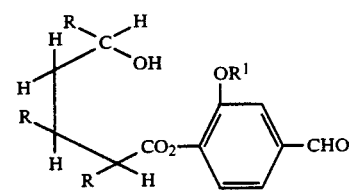

where R is hydrogen or a $C_1$-$C_4$ alkyl substituent; and $R^1$ is methyl or ethyl.

6. A cigarette smoking product in accordance with claim 5 wherein the paper wrapper contains between about 0.01-5 weight percent of flavorant-release additive.

7. A cigarette smoking product in accordance with claim 5 wherein the flavorant-release additive in the paper wrapper is 4,-formyl-2'-methoxyphenyl 5-hydroxy-2-isopropylhexanoate.

8. A cigarette smoking product in accordance with claim 5 wherein the flavorant-release additive in the paper wrapper is 4-'-formyl-2'-ethoxyphenyl 5-hydroxy-2-isopropylhexanoate.

9. A cigarette smoking product in accordance with claim 5 wherein the flavorant-release additive in the paper wrapper is 4'-formyl-2'-methoxyphenyl 5-hydroxy-3-methylhexanoate.

10. A cigarette smoking product in accordance with claim 5 wherein the combustible filler contains between about 0.001-5 weight percent, based on the weight of filler, of a flavorant-release additive corresponding to the formula:

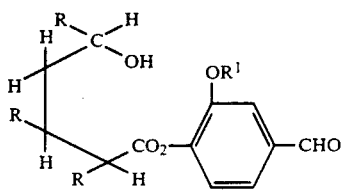

where R is hydrogen or a $C_1$–$C_4$ alkyl substituent; and $R^1$ is methyl or ethyl.

11. A cigarette smoking product in accordance with claim 10 wherein the flavorant-release additive in the combustible filler is 4'-formyl-2'-methoxyphenyl 5-hydroxy-2-isopropylhexanoate.

12. A cigarette smoking product in accordance with claim 10 wherein the flavorant-release additive in the combustible filler is 4'-formyl-2'-ethoxyphenyl 5-hydroxy-2-isopropylhexanoate.

13. A cigarette smoking product in accordance with claim 10 wherein the flavorant-release additive in the combustible filler is 4'-formyl-2'-methoxyphenyl 5-hydroxy-3-methylhexanoate.

14. 4'-Formyl-2'-methoxyphenyl 5-hydroxy-2-isopropylhexanoate.

15. 4'-Formyl-2'-ethoxyphenyl 5-hydroxy-2-isopropylhexanoate.

16. 4'-Formyl-2'-methoxyphenyl 5-hydroxy-3-methylhexanoate.

17. 4'-Formyl-2'-methoxyphenyl 5-hydroxy-2-isopropylhexanoate propyleneglycol acetal.

18. 2-Isopropyl-5-oxohexanoyl chloride.

* * * * *

UNITED STATES PATENT AND TRADEMARK OFFICE
CERTIFICATE OF CORRECTION

PATENT NO. : 5,120,368
DATED : June 9, 1992
INVENTOR(S) : Houminer et al

It is certified that error appears in the above-identified patent and that said Letters Patent is hereby corrected as shown below:

Title page, item [54] and column 1, line 2, "VANILLIN" should be --VANILLYL--.

Col. 10, line 65, "4,-formyl" should be --4'-formyl--.

Col. 1, line 36, "β lactone" should be --γ lactone--.

Col. 6, line 48, "reduoed" should be --reduced--.

Col. 6, line 49, "whioh" should be --which--.

Col. 7, line 36, "H, 9.6" should be --H, 9.62--.

Col. 7, line 65, "in ml" should be --in 50 ml--.

Col. 9, line 67, "ethanbolic" should be --ethanolic--.

Signed and Sealed this

Twenty-first Day of September, 1993

Attest:

BRUCE LEHMAN

Attesting Officer     Commissioner of Patents and Trademarks